United States Patent [19]
Skimming et al.

[11] Patent Number: 5,722,392
[45] Date of Patent: Mar. 3, 1998

[54] BREATHABLE GAS MIXING DEVICES, BREATHING SYSTEMS AND METHODS

[75] Inventors: Jeffrey W. Skimming, Gainesville; Paul B. Blanch, Alachua, both of Fla.

[73] Assignee: University of Florida, Gainesville, Fla.

[21] Appl. No.: 445,442

[22] Filed: May 19, 1995

[51] Int. Cl.⁶ .................................................. A61M 15/00
[52] U.S. Cl. ............................. 128/203.12; 128/203.24
[58] Field of Search ........................ 128/200.18, 200.19, 128/200.21, 203.16, 203.23, 203.24, 204.24, 204.25, 205.11, 911, 912, 203.12

[56] References Cited

U.S. PATENT DOCUMENTS

| | | | |
|---|---|---|---|
| 3,388,705 | 6/1968 | Grosshandler | 128/912 |
| 3,630,196 | 12/1971 | Bird et al. | 128/204.25 |
| 3,913,607 | 10/1975 | Price | 128/205.11 |
| 3,977,432 | 8/1976 | Vidal | 128/205.11 |
| 4,320,754 | 3/1982 | Watson et al. | 128/204.25 |

OTHER PUBLICATIONS

Chapter 8 entitled "Form Resistance" appearing in the book Elementary Mechanics of Fluids by Hunter Rouse and published by John Wiley & Sons, Inc., New York (1960), pp. 252–260.

Primary Examiner—Aaron J. Lewis
Attorney, Agent, or Firm—Saliwanchik, Lloyd & Saliwanchik

[57] ABSTRACT

The present invention relates to gas mixing devices for use with breathing circuit assemblies for use with breathing devices, such as respiratory therapy devices and ventilators and to methods for administering gases, such as breathable gases, like nitric oxide, in combination with other gases in a manner which facilitates the establishment of reliable delivery standards for the gases, which facilitates adequate mixing of the gases, and which reduces exposure time of the gases to one another so as to eliminate or minimize the production of toxic byproducts generated from such gas mixtures.

25 Claims, 10 Drawing Sheets

GAS FLOW DIRECTION

BREATHABLE GAS MIXING DEVICES, BREATHING SYSTEMS AND METHODS

FIELD OF THE INVENTION

The present invention relates to gas mixing devices for use in breathing circuit assemblies and breathing circuit assemblies for use with breathing devices, such as mechanical ventilators and respiratory therapy devices, and to methods for administering gases, such as breathable gases, like nitric oxide, in combination with other gases in a manner which helps to facilitate the development of reliable delivery standards for the mixture of gases, which helps to facilitate adequate mixing of the gases, and which reduces exposure time of the gases to one another so as to eliminate or minimize the production of toxic byproducts generated from such gases being exposed to one another in the mixtures.

BACKGROUND

In various situations which arise in the practice of medicine, it is desirable to administer to subjects breathing gases, such as gaseous medications like nitric oxide, via inhalation to enhance, for instance, pulmonary vasodilation and oxygen levels in blood and to administer other gaseous medications, such as anesthetic gases to induce anesthesia, which is a condition in which patients are entirely unconscious.

A non-anesthetic breathing gas commonly used in such medical application is nitric oxide (NO), ordinarily mixed in suitable proportions with oxygen and/or air. Other breathing gases that may be administered include nitrogen, air, carbon dioxide and the like, and examples of gaseous medications that may be administered to induce anesthesia include nitrous oxide, enflurane, methoxyflurane, chloroform, halothane, isoflurane, etc.

Nitric oxide, however, is not only a therapeutic gas at low concentration levels, but at high concentrations, it is believed to be a toxic gas that is produced by, for example, combustion processes and is a major component of smog. Cigarette smoke contains NO concentrations ([NO]) up to 1000 parts per million (ppm). In both dogs and humans, inhalation of [NO] greater than 15,000 ppm has been reported to cause a rapidly fatal condition involving severe alveolar edema, methemoglobinemia, and hypoxemia. Ironically, inhalation of [NO] less than 100 ppm has recently been suggested to facilitate the medical management of several cardiopulmonary diseases, such as persistent pulmonary hypertension of the newborn, primary pulmonary hypertension, adult respiratory distress syndrome, and neonatal respiratory distress syndrome.

Chemical reactions involving nitric oxide and oxygen and/or air can result in the formation of toxic compound byproducts, such as hydroxyl anions, peroxynitrite, and nitrogen dioxide ($NO_2$). The natural coexistence of nitric oxide and these byproducts complicates the ability to estimate toxicity thresholds for NO and each of these byproduct compounds independently of one another. Estimating toxicity thresholds for both nitric oxide and nitric oxide byproducts is further complicated by potential interactions of exposure duration and compound concentration. Nonetheless, byproduct toxicities, particularly those of $NO_2$ concentration ($[NO_2]$), are believed to predominate over nitric oxide-specific toxicities during nitric oxide inhalation.

In 1988, the National Institute of Occupational Safety and Health (NIOSH) published their recommendations regarding workplace concentration limits on passive exposure to nitric oxide and nitrogen dioxide. The NIOSH recommends limiting the 8-hour time-weighted average [NO] exposure to 25 ppm and the peak [$NO_2$] exposure to 5 ppm. Albeit controversial, some animal studies appear to suggest that [$NO_2$] less than 5 ppm can cause the following: lung histopathology, lowered resistance to infection, reduced growth, and mutagenicity. Mortality rates of both healthy mice and mice infected with bacteria are believed to increase with exposure to [$NO_2$] less than about 5 ppm. Damage to surfactants may result following exposure to about 5 ppm [$NO_2$]. Nitrogen dioxide toxicity, however, appears to be both species and age specific.

Notwithstanding, breathing nitric oxide administered through a mechanical ventilation system differs in at least three ways from passively breathing nitric oxide in the workplace. First, nitric oxide inhaled from a mechanical ventilation system is often associated with supra-ambient oxygen concentrations. Raising oxygen concentrations increases conversion rates of nitric oxide to other toxic byproducts. Second, inhalation of nitric oxide from a mechanical ventilation system necessitates that all of the nitrogen oxides flow through relatively small, confining spaces. Within these spaces, namely ventilator breathing circuits and ventilated airways, variations in concentrations of nitric oxides may exist over relatively short distances. Thus, gas samples from various locations in ventilator breathing circuits may therefore inaccurately represent gases present in the alveoli. On the other hand, samples of gas taken near the face of a subject who is passively inhaling nitric oxide may resemble that subject's alveolar gas contents more closely. Third, accurate [NO] delivery estimates may be confounded by laminar gas flow in a mechanical ventilation system whereas laminar flow is unlikely to confound ambient gas sampling.

A variety of inhaled nitric oxide delivery methods have been described heretofore. See, for example, Wessel, D. L. et al.: *Crit Care Med*, 22:930–938 (1994; Stenquish, O. et al.: *Acta Anaesthesiol Scand*, 37:687–691 (1993); Watkins, D. N. et al.: *Anaesth Intens Care*, 21:861–875 (1993); Tibbals, J. et al.: *Anaesth Intens Car*, 21:844–847 (1993); Channick, R. N. et al.: *Chest*, 105:1843–1847 (1994); and Miller, O. I. et al.: *Arch Dis Child*, 70:F47–49 (1994). Toxic byproduct exposure during nitric oxide inhalation is frequently monitored by measuring [$NO_2$] near the hollow Y-piece. Although the transit time of nitric oxide in the breathing circuits is short, simply bypassing the ventilator housing with the nitric oxide can still result in [$NO_2$] near the hollow Y-piece that exceed 1 ppm.

In view of the above, there are needs for ventilator breathing circuit assemblies for the administration of nitric oxide gas in clinical settings to patients which are safe and effective, and which assure proper mixing of nitric oxide with oxygen and/or air while minimizing exposure time to one another to ensure reliable delivery standards of nitric oxide and to eliminate or minimize the production of nitric oxide toxic byproducts.

SUMMARY OF THE INVENTION

In brief, the present invention overcomes and alleviates certain of the above-mentioned shortcomings and drawbacks associated with the present state of administration of gases, such as nitric oxide, by inhalation through the discovery of simple, durable and efficient gas mixing devices, breathing circuit assemblies and methods for administering safely and effectively to patients gases, such as breathable gases like nitric oxide, and gaseous medications such as anesthetic gases.

Generally speaking, the present invention is directed to compact, lightweight and relatively simple gas mixing devices for use in breathing circuits which are adapted to be connected to hollow breathing tubes or hollow breathing Y-pieces for use with breathing devices, such as ventilators, respiratory therapy devices, scuba equipment, face masks, pressurized suits, etc., and particularly for use with hollow inspiratory tubes that are especially in close proximity to hollow breathing Y-pieces, to restrict the flow of gases flowing therethrough to help facilitate proper mixing of the gases, while minimizing exposure time to one another to facilitate the development of reliable delivery standards of the gases and to eliminate or minimize the production of toxic byproducts generated from such gases. The in-line devices of the present invention may have external dimensions which are approximately the same as those of the internal dimensions of the hollow ventilator inlet hoses or hollow ventilator Y-pieces, not including a sampling port which may optionally be included and used to sample the mixed gases after mixing or an administration port for introducing the gases into the gas mixing devices of the present invention.

A gas mixing device of the present invention may consist essentially of two parts which are formed of lightweight plastic and which remain interconnected or integral with one another throughout use. One part takes the form of a hollow tube or stem connected to the second part which is a hollow cylindrical hub. The device is positioned such that the hollow tube or stem is facing the direction from which the gases are flowing and the hollow hub is facing in a direction opposite that of the hollow tube or stem. The hollow hub in accordance with the present invention may have in one embodiment an external diameter of a size generally equal to that of the internal diameter of a hollow adapter for being received tightly within one end of the adapter. In another embodiment, the hollow hub may have an external diameter approximately equal to that of the hollow breathing inspiratory tubes or hollow breathing Y-pieces. Positioned between the hollow tube or stem and hollow hub is a diaphragm or wall having an aperture therein for permitting the hollow tube or stem to communicate with the hollow hub. The hollow adapter, on the other hand, is generally a cylindrical tube for receiving in one end thereof the hub and having an outer diameter equal to that of the interior of hollow end connectors which connect to hollow breathing inspiratory tubes or a hollow breathing Y-piece or hollow T-piece(s) to form breathing circuit assemblies of the present invention.

Alternatively, the gas mixing devices may be formed with only an aperture in the diaphragm and no hollow stem, thus making the tube or stem optional. While the internal diameter of the hollow stem or aperture may be of any effective size, the internal diameter may be on the order of between about 4 mm and 10 mm, and more preferably between about 4 mm and 7 mm when adults are involved, and about 4 mm when children and infants are involved. It is believed that the Reynold's number and/or drag coefficients of the gases are sufficiently raised as the gases pass through the hollow stem or tube and aperture, or otherwise a restrictor, and into the gas mixing chamber to create enough turbulence in the gas mixing chamber to accomplish adequate mixing of the gases as they pass therethrough. As to the hollow hub, its internal diameter may vary, but generally speaking it may be on the order of between about 8 mm and 22 mm.

When the gas mixing devices of the present invention are inserted into an adapter, a gas mixing chamber is formed between the hollow hub interior and the interior area of the adapter. The length of the gas mixing chamber may be of any suitable size, however, it is preferable for the length of the gas mixing chambers to be about ten times the internal diameter of the stem or tube or aperture.

As to the positioning of the gas mixing device in the breathing circuit assemblies of the present invention, it is preferable to locate the gas mixing devices of the present invention as close to the hollow breathing Y-tubes as possible to minimize contact or exposure time between, for instance, mixtures of nitric oxide and oxygen and/or air. Typically, the gas mixing devices may be positioned within breathing circuit assemblies that are about 1 to about 6 inches from the breathing Y-tubes and more preferably that are about 1 to about 1.5 inches therefrom. It should therefore be understood that the gas mixing devices of the present invention may be positioned in, at or near or made a part of the hollow breathing Y-tube or any suitable distance therefrom, so long as the objectives of the instant invention are not defeated.

Although any gas may be used with the gas mixing devices, breathing circuit assemblies and methods of the present invention, the following description will be made with reference to nitric oxide by way of example. It should also be understood that the terms "gas" and "gases" as used herein should be understood to include vapors, air as well as gases. Moreover, it should be understood that while the gas mixing devices, breathing circuit assemblies and methods of the present invention are described for use in connection with the administration of breathable gases, they also contemplate use for the administration of other unstable gases or gases that require proper mixing when administered together, such as anesthetic gases.

The above features and advantages of the present invention will be better understood with reference to the accompanying Figures, Detailed Description and Examples. It should also be understood that the particular gas mixture devices, breathing circuit assemblies and methods illustrating the present invention are exemplary only and are not to be regarded as limitations of the present invention.

BRIEF DESCRIPTION OF THE FIGURES

37 cm (circle); 10.7 cm (square); 30.2 cm (up-triangle); 60.0 cm (down-triangle); and 102.4 cm (diamond). Nitric oxide flows from the stock cylinder at about 114 ml/min into a corrugated neonatal breathing circuit where it is mixed with nitrogen flowing at about 11,900 ml/min. Assuming that complete mixing occurs, the predicted [NO] is about 19 ppm. Axis range changes and axis scale changes are made to create the graph insert which highlights a selected area of the larger graph. Each data point represents the average of three measurements. Comparison of the curves suggests enhanced gas mixing (less variation in [NO] measurements) with increases in distances between the infusion ports and the sampling port. The relationship between [NO] measurement variations (errors) and the distances can be expressed using the following equation: distance (cm)=31.2−27.8 ($\log_{10}$ [NO]standard deviation)+6.12 ($\log_{10}$[NO]standard deviation)$^2$.

FIG. 6 illustrates improved, yet incomplete, gas mixing with the flow transducer cartridge. Mixing is believed to be more thorough using the diaphragm mixing device.

FIG. 7 illustrates four different nitric oxide delivery methods compared with regard to [$NO_2$] measured at the Y-piece. A corrugated neonatal breathing circuit is used for testing. One method involves infusing nitric oxide 38 cm away from the Y-piece without an in-line mixing device (square). Another method involves infusing nitric oxide 76 cm away from the Y-piece without an in-line mixing device (up-triangle). The diaphragm mixing device method involves infusing the nitric oxide gas 12 cm from the Y-piece (circle). A method involving a pre-breathing circuit blending system is also tested (down-triangle). A nitrogen dioxide measurement difference between the methods of administration is detected (2 way ANOVA F=432.8, df=3, p<0.0001; power with 0.05 α=1.000). Nitrogen dioxide production with both the blending method (p<0.05) and the 76 cm distance method (p<0.05) are higher than the other two methods tested. An interaction effect between the nitric oxide delivery method and the nitric oxide concentration is also detected (p<0.0001).

DETAILED DESCRIPTION

By way of illustrating and providing a more complete appreciation of the present invention and many of the attendant advantages thereof, the following description and examples are given concerning the novel gas mixing devices, breathing circuit assemblies and methods.

Figure 2:
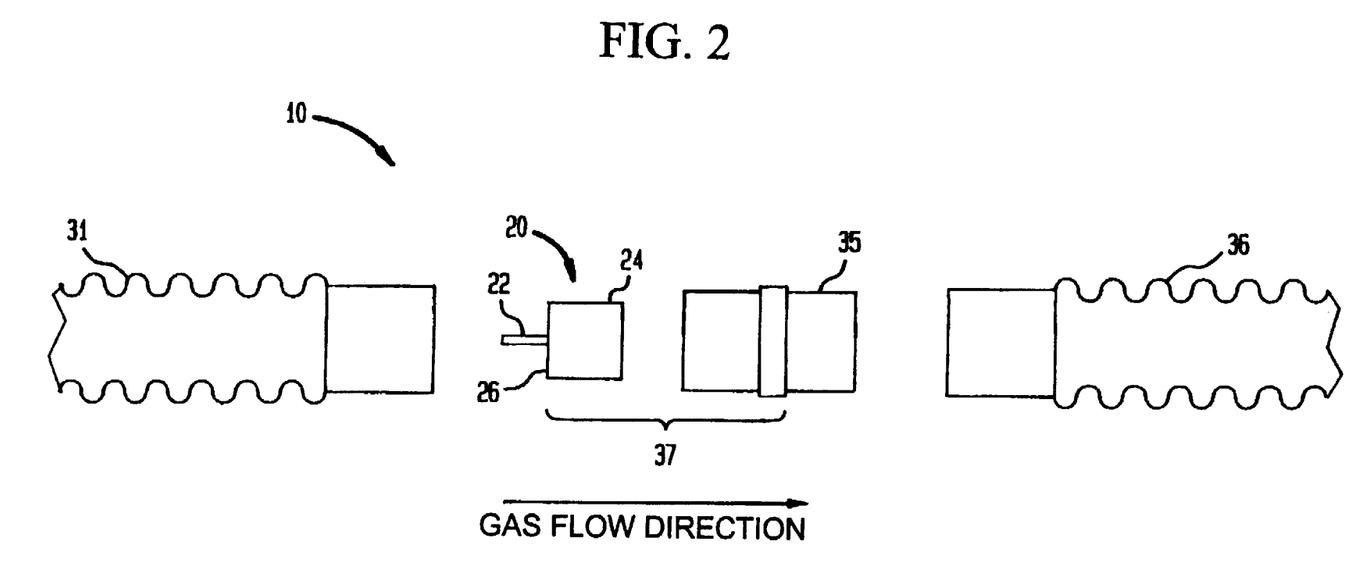
FIG. 2 illustrates a diaphragm mixing device assembly using 22 mm inside diameter breathing circuit. The device adapts to most breathing circuit sizes with minor modifications. A=tubing containing non-mixed nitric oxide gas; B=4.0 mm endotracheal tube hub; C=15 mm inside/22 mm outside diameter adaptor; D=tubing connected to Y-piece.

In FIG. 2, the numeral 10 generally designates a breathing circuit assembly of, for example, a ventilator in accordance with the present invention which comprises a gas diaphragm mixing device 20, a first inspiratory corrugated tube 31 (e.g., ventilator inlet), a hollow adapter 35, and a second inspiratory corrugated tube 36 (e.g., ventilator inlet) connected to a hollow breathing Y-piece (not shown). The breathing circuit assembly 10 is shown with a 22 mm internal diameter. More particularly, adapter 35 is provided with an internal diameter of 15 mm and an outer diameter of 22 mm. The gas diaphragm mixing device 20 consists essentially of a forward hollow stem or tube portion 22 and a rearwardly disposed hollow hub portion 24. Intermediate between these two portions is a diaphragm or wall 26 having an aperture therein (not shown) in communication with the hollow stem or tube portion 22 for permitting the gases to flow through the stem a tube portion 22 and the aperture in diaphragm 26 and into the hub portion 24.

When a gas diaphragm mixing device 20 is snugly inserted into one end of adapter 35, a gas mixing chamber 37 is formed by the hollow interiors of hub portion 24 and adapter 35. Moreover, when the gas diaphragm mixing device 20 is assembled into breathing circuit assembly 10 and gases flow in the direction as shown in FIG. 2, it is believed that, under the usual conditions of breathing gases through a hollow inspiratory tube (i.e., flow rates and velocities of the gases), the narrowing or restriction of the gas passageway through the breathing circuit assembly 10 caused by the stem or tube portion 22, the diaphragm 26 and the aperture in the diaphragm 26 will result in the Reynold's number and/or drag coefficients being increased for the gases to create sufficient turbulence in the gas mixing chamber 37, so that the gases passing into the gas mixing chamber 37 are adequately mixed prior to entering into the second hollow inspiratory corrugated tube 36.

Figure 10A:
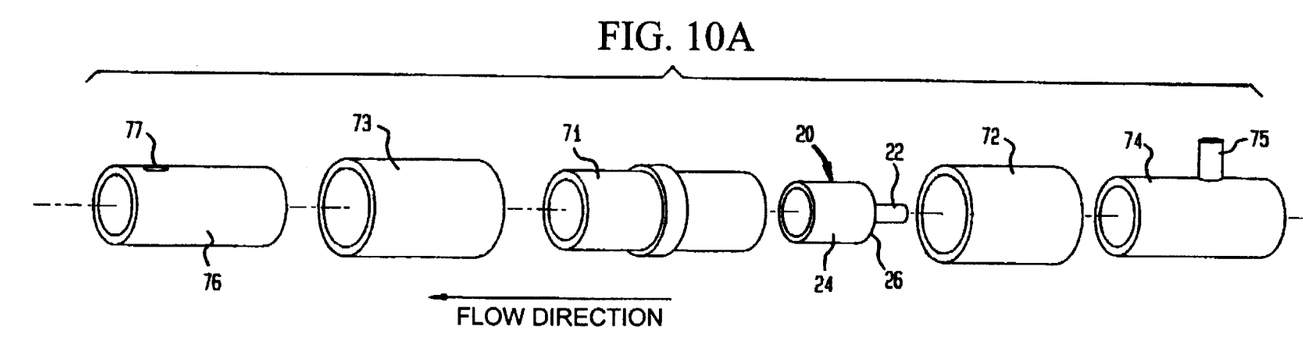
FIGS. 10A and 10B depict an exploded view of the breathing circuit assembly of the diaphragm gas mixing device illustrated in FIG. 2.
Figure 10B:
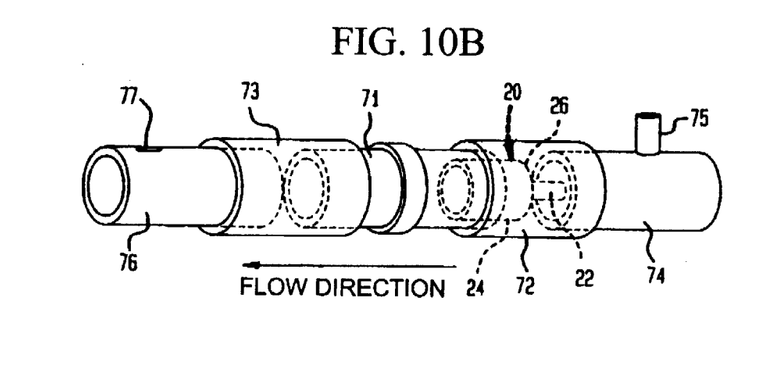
Figure 11A:
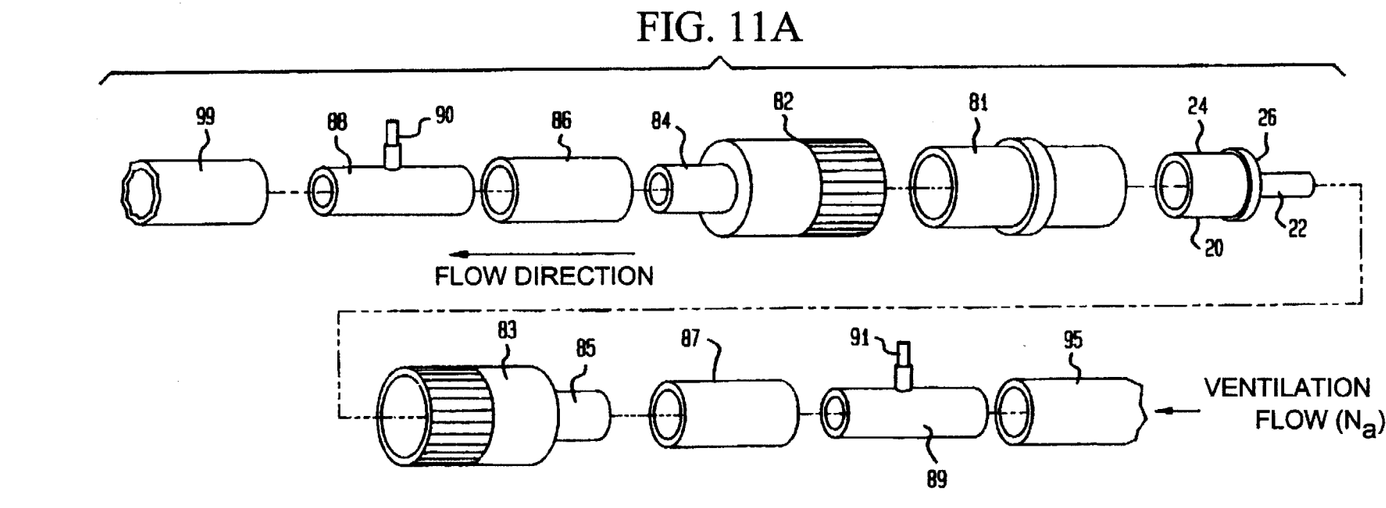
FIGS. 11A and 11B depict an exploded view of a further breathing circuit assembly of the diaphragm mixing device as shown in FIG. 2.
Figure 11B:
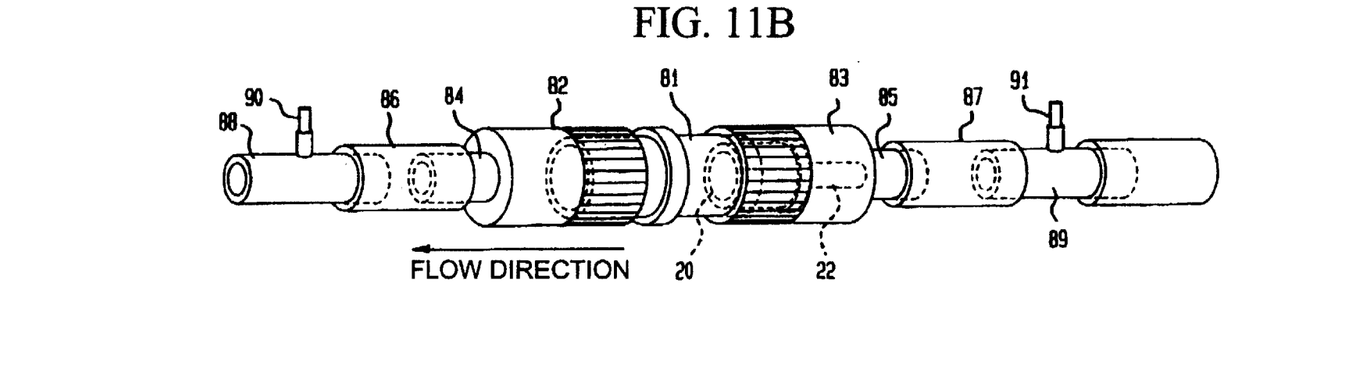

To reduce contact time between oxygen and/or air and nitric oxide when nitric oxide is selected as the breathing gas of choice, an optional delivery port for nitric oxide, such as in the form a hollow T-piece, may be provided in a first hollow inspiratory tube 31 or between a first hollow inspiratory tube 31 and the gas diaphragm mixing device 20, such as shown in FIGS. 10 and 11, respectively.

As indicated hereinabove, the gas diaphragm mixing device, such as shown generally at 20, of the present invention may be formed with a lightweight, inexpensive plastic material and the internal diameters of the hollow tube or stem portion 22 and the aperture may range from between about 4 mm to about 10 mm or more. Preferably, however, when breathing circuit assembly 10 is for use with adults, the internal diameters of the hollow stem or tube portion 22 and/or the aperture are on the order of between about 4 mm and about 7 mm, and for infants and pediatric patients, they are about 4 mm. While it is preferred that the internal diameter of the stem or tube be equal to that of the aperture in the diaphragm, it should be understood that it is not required.

As also indicated above, to create enough turbulence and adequate gas mixing, the length of the gas mixing chamber 37 should be approximately ten (10) times the size of the internal diameters of the stem or tube portion 22 or the aperture. Thus, the combination of the length of the interiors of the hub portion 24 and adapter 35 form the length of the gas mixing chamber 37. Therefore, the length of the interior of the hub portion 24 and the internal area of the adapter 35 should preferably, but not necessarily, be at least equal to 10 times the internal diameter of the stem or tube portion 22 or aperture in diaphragm 26. Notwithstanding, any gas mixing chamber having other lengths and internal diameters than those set forth herein that accomplish adequate mixing is contemplated by the present invention. Moreover, while the gas mixing chamber 37 as described herein in FIG. 2 is formed by the interior space of hub portion 24 and adapter 35, it should be appreciated that it may be formed by other components or structures or modifications to hub portion 24, and such alternatives are contemplated by the present invention. See, for example, FIGS. 8A–C and 9A–C.

Also in accordance with the present invention, the internal diameter of the gas mixing chamber 37 may vary. However, it is believed that the internal diameter of the mixing chamber is preferably about 22 mm and the internal diameter of the hub portion 24 is preferably about 13 mm.

Figure 8A:
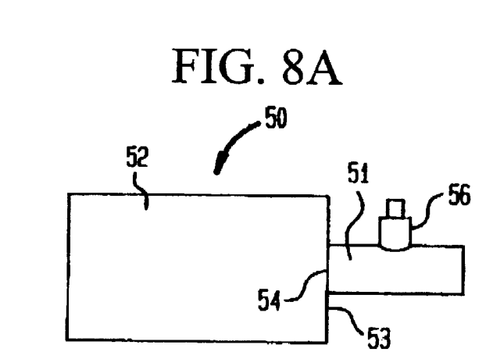
FIGS. 8A, 8B and 8C depict an alternative gas diaphragm mixing device in accordance with the present invention.
Figure 8B:
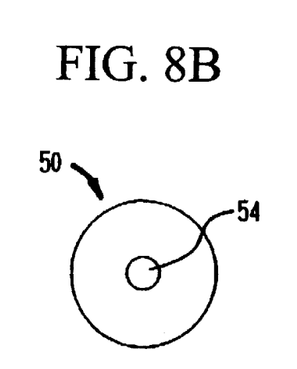
Figure 8C:
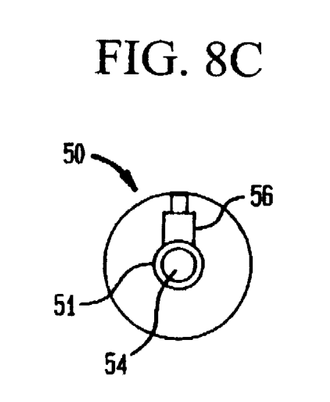

In the alternative, gas diaphragm mixing device 20, as shown in FIG. 2, may be utilized without stem or tube portion 22 to achieve the results contemplated by the present invention. See Example II. Also as an alternative, other gas mixing devices contemplated by the present invention include those illustrated in FIGS. 8–9. As shown in FIGS. 8A, 8B and 8C, numeral 50 generally depicts an alternative gas diaphragm mixing device in accordance with the present invention which comprises a gas receiving chamber 51, a hollow hub or a gas mixing chamber 52 and a diaphragm or wall 53 having an aperture 54 positioned therebetween. In addition, the gas diaphragm mixing device 50 further includes a stem 56 for introducing a gas, such as a breathable gas like nitric oxide, into receiving chamber 51. As the flow arrows indicate in FIG. 8, when the gases flow from gas receiving chamber 51 and into gas mixing chamber 52, turbulence is created in gas mixing chamber 52 for thoroughly mixing the gases passing therein. The gas diaphragm mixing device 50 also includes receiving connector 57 and exiting connector 58 for connecting to hollow inspiratory tubes and/or hollow breathing Y-piece. In accordance with this alternative embodiment, it should be appreciated that the hollow hub 52 is the gas mixing chamber.

Figure 9A:
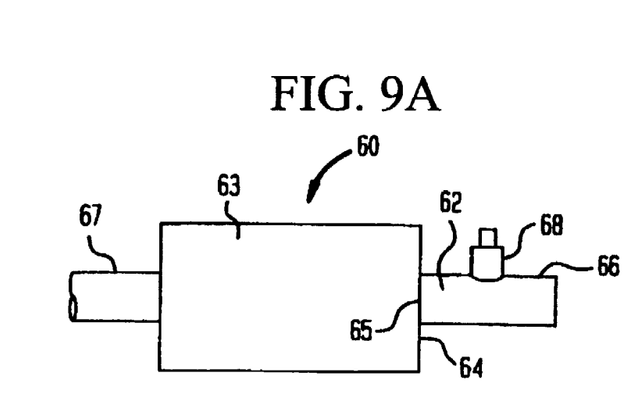
FIGS. 9A, 9B and 9C depict a further gas diaphragm mixing device as contemplated by the present invention.
Figure 9B:
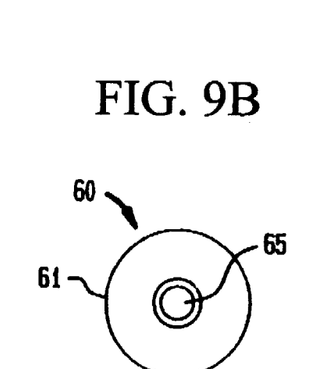
Figure 9C:
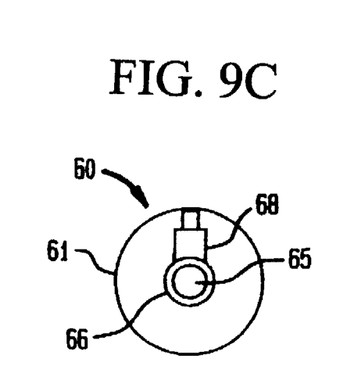

In yet a further alternative device contemplated by the present invention, a gas diaphragm mixing device is depicted in FIGS. 9A, 9B and 9C and is generally designated at numeral 60. Gas diaphragm mixing device 60 generally comprises a hollow body or hub 61 divided into a gas receiving chamber or stem 62 and a gas mixing chamber 63 by diaphragm or wall 64. Diaphragm 64 further includes an aperture 65 for permitting the gases to flow from gas receiving chamber 62 into gas mixing chamber 63. Gas diaphragm mixing device 60 further includes receiving connector 66 and exiting connector 67 for connecting gas diaphragm mixing device 60 to hollow inspiratory tubes and/or a hollow breathing Y-piece. As further illustrated in FIG. 9, the receiving connector 66 further includes an administration port 68 for introducing a gas or gases of choice, such as a breathable gas like nitric oxide, into gas receiving chamber 62.

In view of the alternatives described herein, and illustrated in FIGS. 8A–C and 9A–C, it should be understood by those versed in this art that other suitable designs may be employed to take advantage of the use of an apertured diaphragm or flow restriction to increase the Reynold's number and/or drag coefficients of the gases as they pass into gas mixing chambers to generate sufficient turbulence in the gas mixing chambers to accomplish the objectives of the present invention. Moreover, other constructions, alternative to the use of apertured diaphragms, may be employed. For example, gas mixing devices employing non-pressure restrictive baffles or gas mixing devices utilizing gas mixing chambers equipped with moving parts, such as a gas mixing chamber with floating balls positioned therein, or gas mixing devices having chambers provided with a flow transducer therein, such as a Bird's Flow Transducer Cartridge, Part No. 9230, Palm Springs, Calif., referenced in Example I hereinafter, and TVX Flow Transducer Cartridge, Stock No. 237-2228-870, distributed by Ohmeda, Louisville, Colo., may be utilized. Still further, it should be understood that the gas mixing chamber may be of any suitable form or construction, such as it may be formed by that portion of the interior of a hollow inspiratory tube which follows a flow restrictor. Thus, it should be readily apparent to those versed in this art that the present invention contemplates any gas mixing device which has the ability to accomplish the objectives of the present invention, i.e., adequate mixing of all gases being administered with minimal exposure time to one another to facilitate the development of reliable delivery standards and to eliminate or minimize toxic byproducts which may be formed from mixtures of gases, and especially mixtures of unstable gases, due to prolonged contact times therebetween.

Use of the diaphragm gas mixing device illustrated in FIG. 2 is depicted in breathing circuit assemblies shown in FIGS. 10A & B and 11A & B. As shown in FIGS. 10A & B, the numeral 70 generally references a breathing circuit which includes gas mixing device 20 of FIG. 2. As further shown in FIGS. 10A & B, gas mixing device 20 is connected at one end to hollow adapter 71. Hollow adapter 71 is connected at each end thereof to hollow connectors 72 and 73 for connecting the gas mixing device 20 to a hollow T-piece 74 and a hollow inspiratory tube 76. Hollow inspiratory tube 76 is equipped with a sample port 77 for sampling the mixed gases after they pass through gas mixing device 2. Hollow T-piece includes an administration port 75 for introducing a gas, such as a breathable gas like nitric oxide, into the flow of gases such as oxygen and/or air prior to gas entry into gas mixing device 20. As depicted, the breathing circuit assembly 70 as shown in FIGS. 10A & B has an internal diameter of about 22 mm and the stem or tube 22 of gas mixing device 20 has an internal diameter of 4 mm.

With respect to the breathing circuit assembly generally indicated at 80 in FIGS. 11A & B, it too comprises the diaphragm gas mixing device 20 of FIG. 2. The gas mixing chamber or hub 24 of gas mixing device 20 as shown in FIG. 11 has an outer diameter of 22 mm and an inner diameter of 15 mm. Also as shown in FIGS. 2 and 11, the gas mixing device 20 is equipped with a hollow stem 22 having an internal diameter of 4 mm. The breathing circuit assembly of FIGS. 11A & B further includes a hollow adapter 81 having an internal diameter of about 22 mm for receiving gas mixing device 20 at one end thereof. Also included with breathing circuit assembly 80 are two end connectors 82 and 83. Each end connector 82 and 83 are designed to snugly receive one end of hollow adapter 81. End connectors 82 and 83 are also equipped with hollow fittings 84 and 85. Connected to hollow fitting 84 is hollow inlet tubing 86 and connected to hollowing fitting 85 is hollow inlet tubing 87. Connected to hollow inlet tubing 86 is a hollow T-piece 88 equipped with a sampling port 90, and connected to hollow inlet tubing 87 is a hollow T-piece 89 equipped with a gas administration port 91. Connected to hollow T-piece 88 and hollow T-piece 89 are hollow inspiratory tubes 99 and 95, respectively. Sample port 90 downstream from gas mixing device 20 provides access to the interior of the breathing circuit assembly 80 for sampling the mixed gases exiting from the hollow adapter 81, while administration port 91 upstream from gas mixing device 20 allows for the introduction of a gas, such as a breathable gas like nitric oxide, immediately before the mainstream gases flowing therein from hollow inspiratory tube 95 enter gas mixing device 20.

In use, the gas mixing devices and breathing circuit assemblies of the present invention uniquely provide for adequate mixing of multiple gases being inhaled by subjects via breathing devices, such as respiratory therapy devices and ventilator systems. Moreover, the gas mixing devices and breathing circuit assemblies of the present invention uniquely and advantageously allow for the gases to be mixed and a certain gas or gases to be introduced into the breathing devices in close proximity to the subjects undergoing treatment to facilitate the development of reliable delivery standards for the mixtures of gases being administered, to facilitate adequate mixing of such gases and to shorten contact or exposure time of the gases between one another to minimize or eliminate the number of toxic byproducts being formed from such gas mixtures.

The present invention will now be further illustrated with reference to the following examples.

EXAMPLE I

A stock cylinder containing 1986 ppm nitric oxide gas is prepared by Alphagaz (LaPorte, Tex.) with the balance being nitrogen gas. The stock cylinder is prepared using chemiluminescence techniques and standards referenced to those of the National Institute of Standards and Technology. the stock cylinder also contains 7 ppm of nitrogen dioxide.

Figure 1:
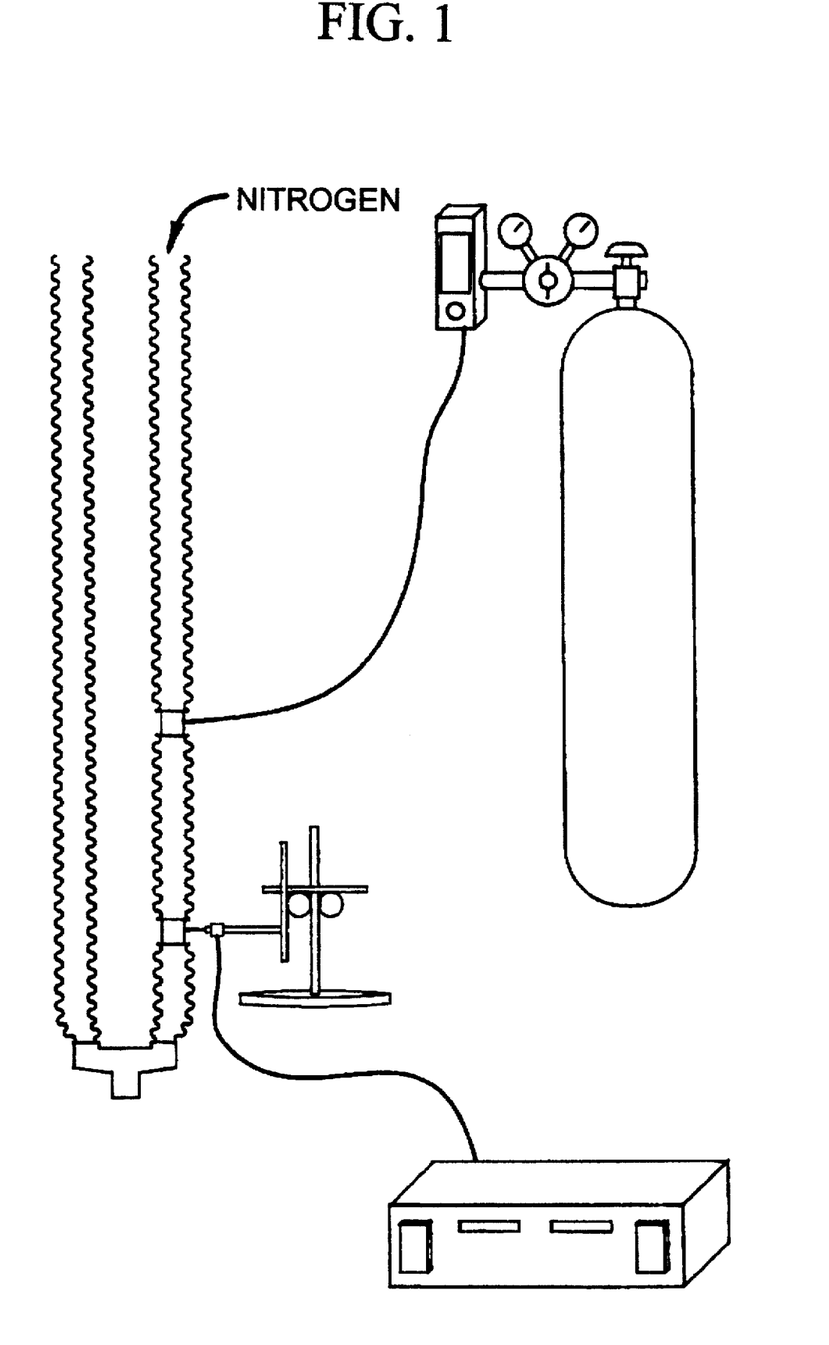
FIG. 1 is a schematic illustrating an example of a basic design for a nitric oxide apparatus of the present invention. Variations of this basic design are used to test the influences of stock nitric oxide flow, tubing distance, tubing shape, and mixing devices on mixing thoroughness.

Three different types of ventilator breathing circuits are used: corrugated neonatal (Hudson, California), smooth-bore (Tygon) neonatal (Norton Performance Plastics, Ohio), and corrugated adult (TPI Medical Products, Illinois). The neonatal circuits both have 10 mm internal diameters (i.d.) and the adult circuit has a 22 mm i.d. Nitric oxide is infused into the breathing circuit inspiratory limbs using T-connectors. A 10 mm outside diameter (o.d.)×10 mm o.d. connector with a 4.5 mm o.d./3.0 mm i.d. hose barb (Ackrad Laboratories, New Jersey) is placed in-line when using the neonatal tubing. A 22 mm o.d.×22 mm o.d. connector is custom fitted with a 4.5 mm o.d./3.0 mm i.d. hose barb and placed in-line when using the adult tubing. A nitrogen-calibrated flowmeter is used to deliver nitrogen as the primary gas flowing through the breathing circuit. Nitrogen-calibrated flowmeters are also used to deliver precise nitric oxide flow rates. All gases flow through the breathing circuits at about 22° C. A schematic of both the breathing circuit and the gas sampling setup is shown in FIG. 1.

Nitric oxide concentration variations across the inspiratory tubing diameter are measured using a model 2108 Dasibi chemiluminescence nitrogen oxides analyzer (Glendale, Calif.). These variations are presumed to reflect gas streaming. A 20 gauge stainless steel needle is attached to the sampling port of the nitrogen oxides analyzer using 80 cm of 4.8 mm i.d. Tygon tubing. The needle is positioned through gas-tight seals placed in the breathing circuit tubes. Using a micromanipulator and beginning at the ipsilateral wall, the needle is positioned in millimeter increments across the tubing's cross sectional diameter. Sampling ports and delivery ports are located in ipsilateral alignment along the tube's axis.

Nitric oxide flows from the stock cylinder into pure nitrogen flowing at about 9600 ml/min through the corrugated neonatal breathing circuit. The flow rates (and predicted resultant [NO]) are about 55 m/min (11 ppm), about 114 ml/min (23 ppm), about 170 ml/min (35 ppm), and about 231 ml/min (47 ppm). Nitric oxide concentrations are measured across the tubing diameter 3.7 cm from the infusion port. For each flow rate, a standard deviation is calculated using the respective set of ten [NO] measurements.

The effects of sampling port to infusion port distances on [NO] variations are assessed using the following distances away from the sampling port: 3.7 cm, 10.7 cm, 30.2 cm, 60 cm and 102.4 cm. Nitric oxide flows from the stock cylinder at about 114 ml/min into pure nitrogen flowing through the corrugated neonatal circuit at about 11,900 ml/min to yield a predicted [NO] of 19 ppm. For each infusion port to sampling port distance, [NO] is measured across the tubing diameter and a standard deviation of these measurements is calculated.

Streaming characteristics of corrugated versus smooth tubing are compared using the neonatal breathing circuits. Gases are sampled across the tubing diameters at 21.3 cm from the nitric oxide infusion port. Nitric oxide flows at a rate of about 104 ml/min from the stock cylinder into nitrogen flowing at about 10,600 ml/min yielding a predicted [NO] of 19 ppm. Standard deviations of [NO] for each tubing style are estimated.

A diaphragm-type mixing device is constructed, see FIG. 2, using parts that are commonly available in hospital settings. The basic design entails seating an endotracheal tube hub (Mallinckrodt Anesthesiology Division, Missouri) in a 15 mm i.d./22 mm o.d. adapter (Hudson, California). The device is positioned directly in-line when using the adult breathing circuit. Two 22 mm i.d. to 10 mm o.d. adapters (Hudson, Calif.) are used to interpose the diaphragm mixing device into the neonatal breathing circuits. The endotracheal tube hub flanges are trimmed so that the hub fits snugly inside 22 mm i.d. tubes or the 22 mm i.d. to 10 mm o.d. adapters. Other endotracheal tube hubs which possess similar flow characteristics if the shapes of the hubs are similar (particularly the flat transition from the large cylindrical position to the small cylindrical portion) may be used as substitutes. As an alternative, the smaller cylindrical portion of the hub may be removed without any significant changes in gas mixing efficacy.

The effects of endotracheal tube hub sizes and the effects of oxygen flow rates on the inspiratory limb gas pressure (on the ventilator side of the mixing device) are tested using the corrugated neonatal breathing circuit. The mixing device is placed in the inspiratory limb next to the Y-piece. The circuit is left unpressurized (wide open) beyond the Y-piece. Hubs from endotracheal tubes ranging from 2.5 mm to 5.5 mm are positioned in the mixing device one at a time. Pure oxygen flowed through the breathing circuit at the following rates: about 2 l/min, about 4 l/min, about 8 l/min, about 10 l/min, about 12 l/min, about 15 l/min, about 20 l/min, about 30 l/min, about 40 l/min, about 60 l/min and about 70 l/min.

Partial flow obstruction of breathing circuits caused by interposition of the mixing device affects ventilator function in a manner that resembles kinking of breathing circuit tubing. Both manufacturer specifications and these trials reveal that the following constant flow ventilators (Healthdyne; Marietta, Ga.), VIP Bird (Bird Products Corporation, California), Baby Bird (Bird Products Corporation, California), Infant Star (Infrasonics, California), Bear Cub (Bear Medical Systems, California), Sechrist (Sechrist Industries, California) tolerate a pressure gradient from the inspiratory to the expiratory side up to at least about 12 cm $H_2O$. Also, 4.0 mm endotracheal tube hubs provide thorough gas mixing at flow rates as low as about 2 l/min and cause pressure gradients exceeding about 12 cm $H_2O$ only when gas flow rates exceed about 30 l/min.

A mixing device constructed with a 4.0 mm endotracheal tube that is compatible with these constant flow ventilators is determined by studying the effect of running each ventilator with the mixing device. A corrugated neonatal breathing circuit is connected to a test lung for this purpose and machines are run at least 60 minutes. In an attempt to maximize the likelihood of triggering alarms or detecting changes in volume characteristics, the following setting ranges for testing compatibility are utilized: flow, about 5–30 l/min; rate, about 10–100 breaths per minute; inspiratory time, about 0.1–1.0 seconds; peak inspiratory pressure, about 10–60 cm $H_2O$; end expiratory pressure, about 0–20 cm $H_2O$. When variations in one setting are being tested, the basic setting in ventilatory parameters are left at the maximum value for the range of values tested.

Variations in [NO] along the tubing's cross sectional diameter are measured 12 cm from the nitric oxide infusion port under the following different conditions: without a mixing device, using a flow transducer cartridge (Bird Products Corporation, Part No. 9230, Palm Springs, Calif.), and with a diaphragm mixing device. This flow transducer cartridge is designed to fit into a 22 mm i.d. (adult) breathing circuit. It is thought that mixing occurs as the gases pass through the device due to the fact that the device contains two baffles and a propeller apparatus in series. The corrugated adult breathing circuit is used for testing. Nitric oxide flows from the stock cylinder at about 150 ml/min into nitrogen flowing at about 9800 ml/min yielding a predicted [NO] of about 30 ppm.

Four different nitric oxide delivery methods are compared to each other with regard to [$NO_2$] being measured at the Y-piece. Nitrogen dioxide measurements are made using an electrochemical analyzer (Drager Inc., Virginia). A corrugated neonatal breathing circuit is used for testing. One method involves infusing nitric oxide 38 cm away from the Y-piece without an in-line mixing device. Another method involves infusing nitric oxide 76 cm away from the Y-piece without an in-line mixing device. The diaphragm mixing device method involves infusing the nitric oxide gas 12 cm from the Y-piece. Also under consideration is a method involving a pre-breathing circuit blending system that is modeled after a basic design by Wessel and colleagues. See Wessel, D. L. et al.: Crit Care Med, 22:930–938 (1994). For the pre-breathing circuit blending method, nitric oxide is first mixed with oxygen in a low flow blender (Bird Products Corporation, California). From the low flow blender, the gases flow through 65 cm of 6.4 mm i.d. tubing into a humidifier (Hudson-RCI, Arlington Heights, Ill.) with a full water reservoir and then through the full length (125 cm) of the breathing circuit inspiratory limb. Three independent [$NO_2$] measurements are made at the Y-piece using each of the four methods and using each of the following [NO]: about 6 ppm, about 10 ppm, about 16 ppm, about 25 ppm, about 40 ppm, about 63 ppm, about 85 ppm, and about 100 ppm.

For each lumina position, three independent [NO] measurements are obtained. The three readings are averaged resulting in 10 mean measurements for the neonatal (10 mm i.d.) tubing and 18 mean measurements for the adult (22 mm i.d.) tubing. Slight protrusion of the gas-tight seal in the 22 mm i.d. tubing prohibits obtaining measurements from the first four millimeters on the proximal (or ipsilateral) side of the cross sectional diameter of this tubing. Errors of [NO] delivery estimates are determined by calculating standard deviations of either the 10 mean measurements or the 18 mean measurements corresponding with the tubing diameters. Polynomial regression analysis is used to correlate [NO] delivery estimate errors with the delivery port to sampling port distances. The relationship between [$NO_2$] measurements and both [NO] and delivery method is analyzed using a two factor analysis of variance test. Pairwise multiple comparisons are analyzed using the Studen-Newman-Keuls methods.

Figure 3:
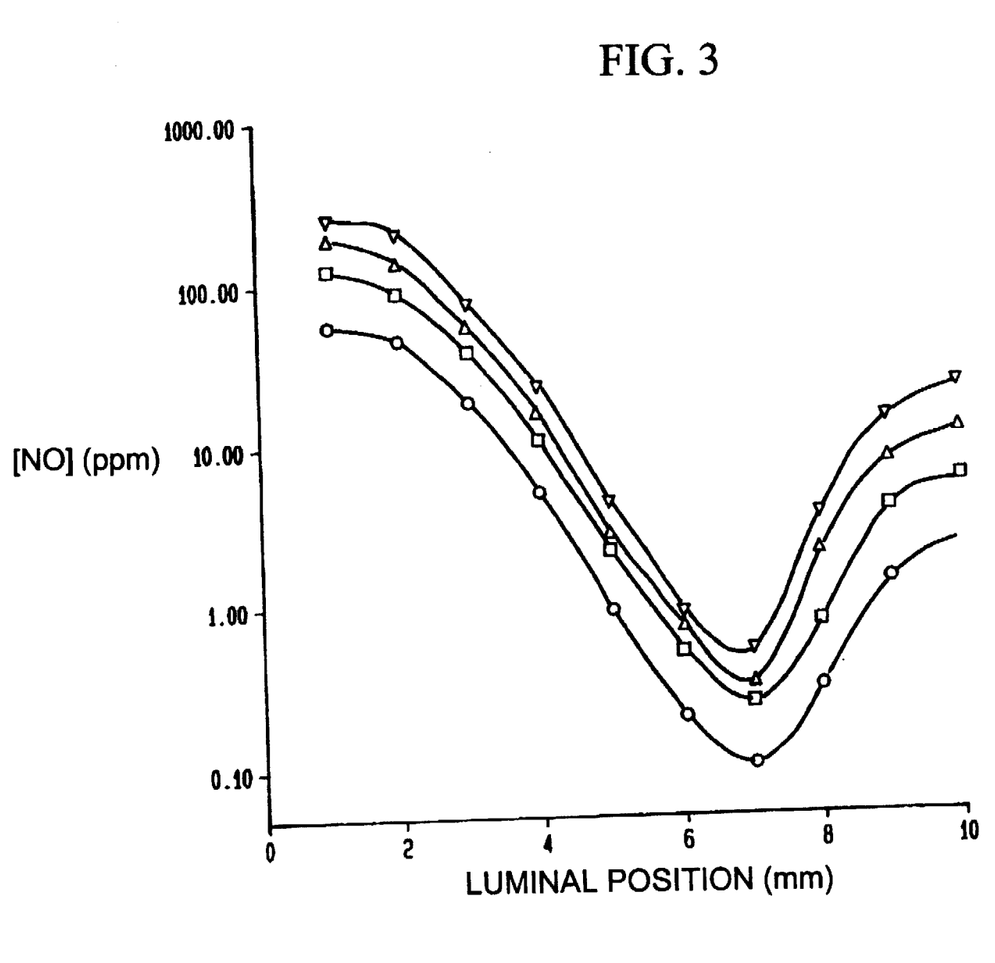
FIG. 3 illustrates nitric oxide concentrations ([NO]) varying with respect to sampling needle position along the cross sectional diameter of 10 mm inside diameter corrugated breathing circuit tubing. The sampling part is located 3.7 cm away from the nitric oxide infusion port. Stock nitric oxide is infused into nitrogen flowing through the inspiratory limb of the breathing circuit at 9600 ml/min. Four different infusion flow rates are tested: 55 ml/min (circle); 114 ml/min (square); 170 ml/min (up-triangle); and 231 ml/min (down-triangle). Assuming that complete mixing occurred, the predicted [NO] are: 11 ppm, 23 ppm, 35 ppm, and 47 ppm, respectively.

Nitric oxide concentrations vary according to the sampling position along the tubing's cross sectional luminal diameter. See FIG. 3. the mean measurement of [NO] ±standard deviation (and predicted [NO] assuming complete mixing) are as follows: 60±92 ppm (47 ppm), 42±67 ppm (35 ppm), 27±43 ppm (23 ppm), 13±20 ppm (11 ppm). The mean $\log_{10}$ [NO]±standard deviations are as follows: 1.12±0.92 ppm, 0.93±0.93 ppm, 0.72±0.94 ppm, 0.36±0.97 ppm. Both the similarities of the $\log_{10}$ [NO] standard deviations and the parallel nature of the curves in FIG. 3 indicate that the [NO] measurement errors may be independent of the NO flow rates with commonly used flow rates, but dependent upon the luminal position of the sampling needles. For each nitric oxide flow rate which is tested, the highest [NO] is close to the tubing wall ipsilateral to the infusion port. The lowest concentration of gas is consistently measured at a point between the tubing axis and the contralateral tubing wall with an arrangement consistent with FIGS. 1 and 2. A small rise in the [NO] is found near the tubing wall contralateral to the infusion port.

Figures 4A, 4B:
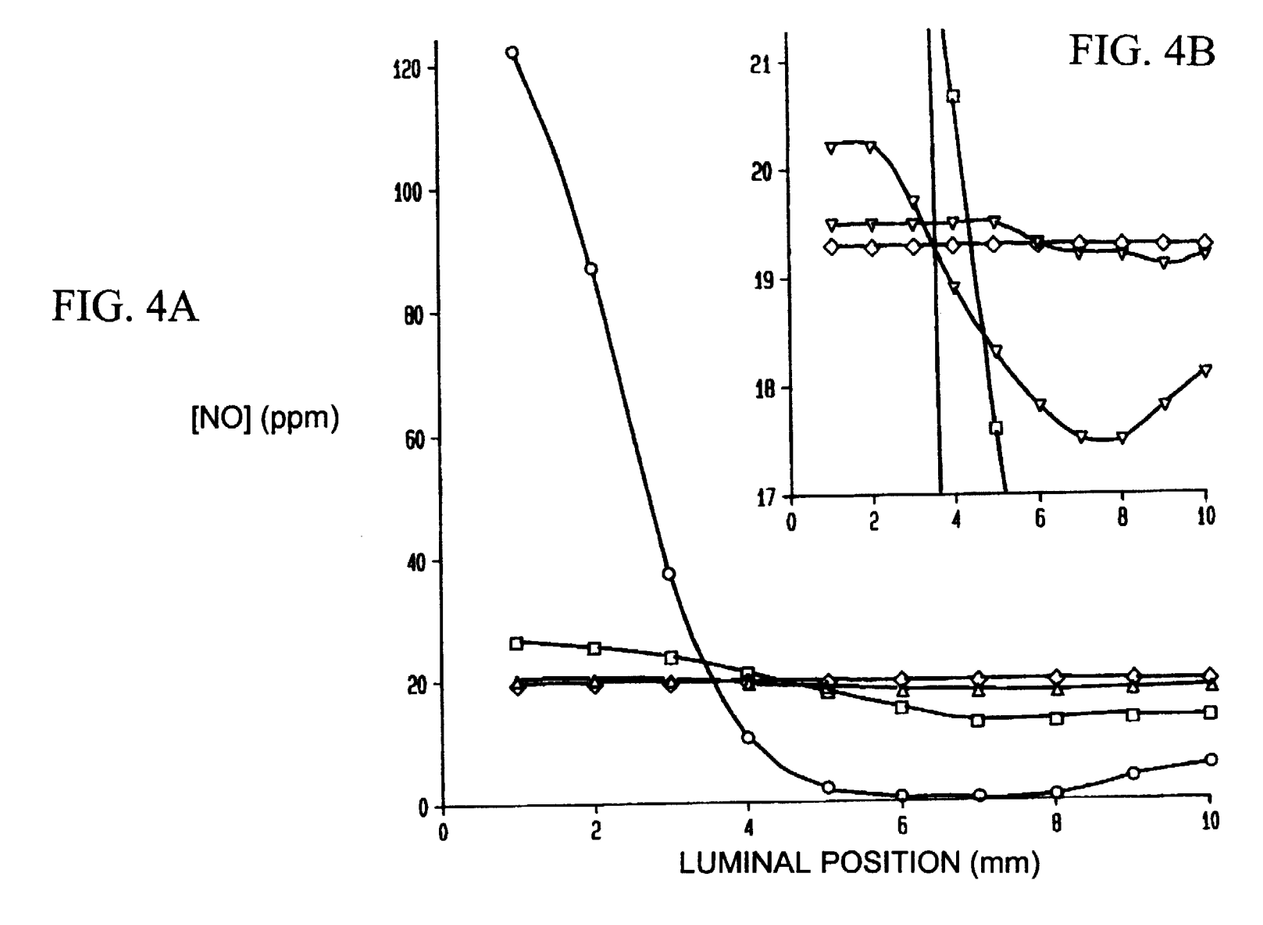
FIG. 4 illustrates the result of sampling for nitric oxide concentration ([NO]) analysis which is performed at the following distances away from the nitric oxide infusion port.

Variations in [NO] are decreased with increased infusion port to sampling port distances. See FIG. 4. The mean measurement of [NO]±standard deviation (respective infusion port to sampling port distances) are as follows: 26.95±43.18 ppm (3.7 cm), 18.03±5.40 ppm (10.7 cm), 18.60±1.08 ppm (30.2 cm), 19.35±0.16 ppm (60.0 cm), 19.30±0.01 ppm (102.4 cm). The relationship between infusion port to sampling port distances and [NO] standard deviations can be described using the following equation in which s.d.=standard deviation, $r^2=0.996$, $F=245$, and $p<0.01$:

$$\text{distance }(cm)=31.2-27.8\ (\log_{10}\ [NO]s.d.)+6.12\ (\log_{10}\ [NO]s.d.)^2.$$

Nitric oxide concentrations are measured along the cross sectional diameter of both smooth and corrugated tubing are shown in Table 1. The mean measurement of [NO]±standard deviation are as follows: 16.75±3.68 ppm (smooth) and 18.06±2.01 ppm (corrugated). The lower standard deviation with corrugated tubing indicates that the corrugations augment mixing.

Figures 5A, 5B:
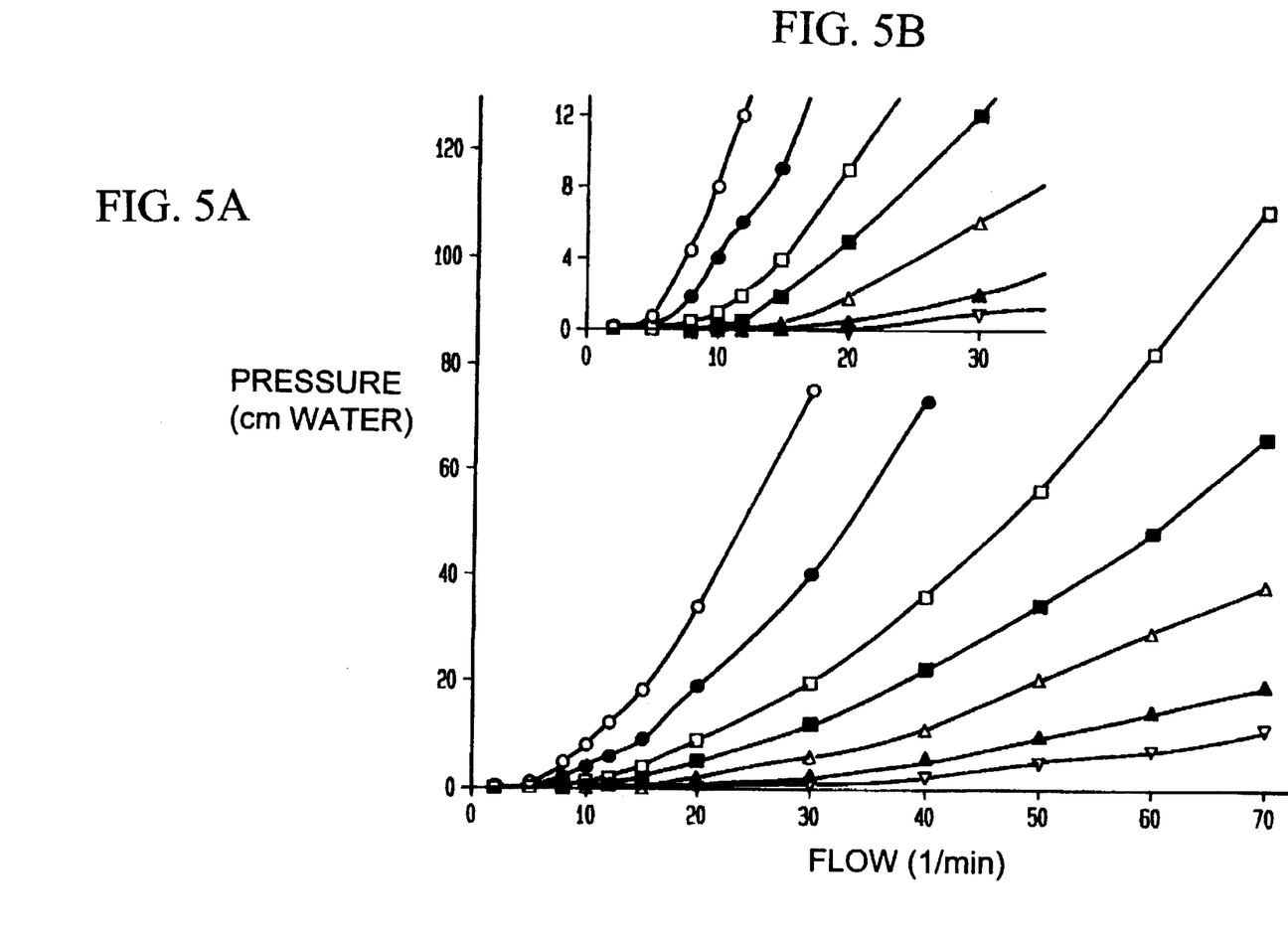
FIG. 5 illustrates endotracheal tube hub size effects and oxygen flow rate effects on the inspiratory limb gas pressure (on the ventilator side of the mixing device). A corrugated neonatal breathing circuit is used for testing. The hub sizes tested are as follows: 2.5 mm (circle); 3.0 mm (filled circle); 3.5 mm (square); 4.0 mm (filled square); 4.5 mm (up-triangle); 5.0 mm (filled up-triangle); 5.5 mm (down-triangle). Axis range changes and axis scale changes are made to create the graph insert which highlights a selected area of the larger graph. For each hub size tested, increasing the oxygen flow rate results in higher pressure measurements. For each oxygen flow rate tested, increasing the hub size results in lower pressure measurements.

The inspiratory limb gas pressures are measured with various hub sizes and oxygen flow rates are shown in FIG. 5. For each hub size tested, increasing the oxygen flow rate results in higher pressure measurements. For each oxygen flow rate tested, increasing the hub sizes result in lower pressure measurements. In-line testing o the diaphragm mixing device indicate that the device (with a 4.0 mm endotracheal tube hub) is compatible with each ventilator tested within the range of ventilation parameters tested. No mechanical malfunctions are detected, and no inadvertent alarms are triggered.

Figures 6A, 6B:
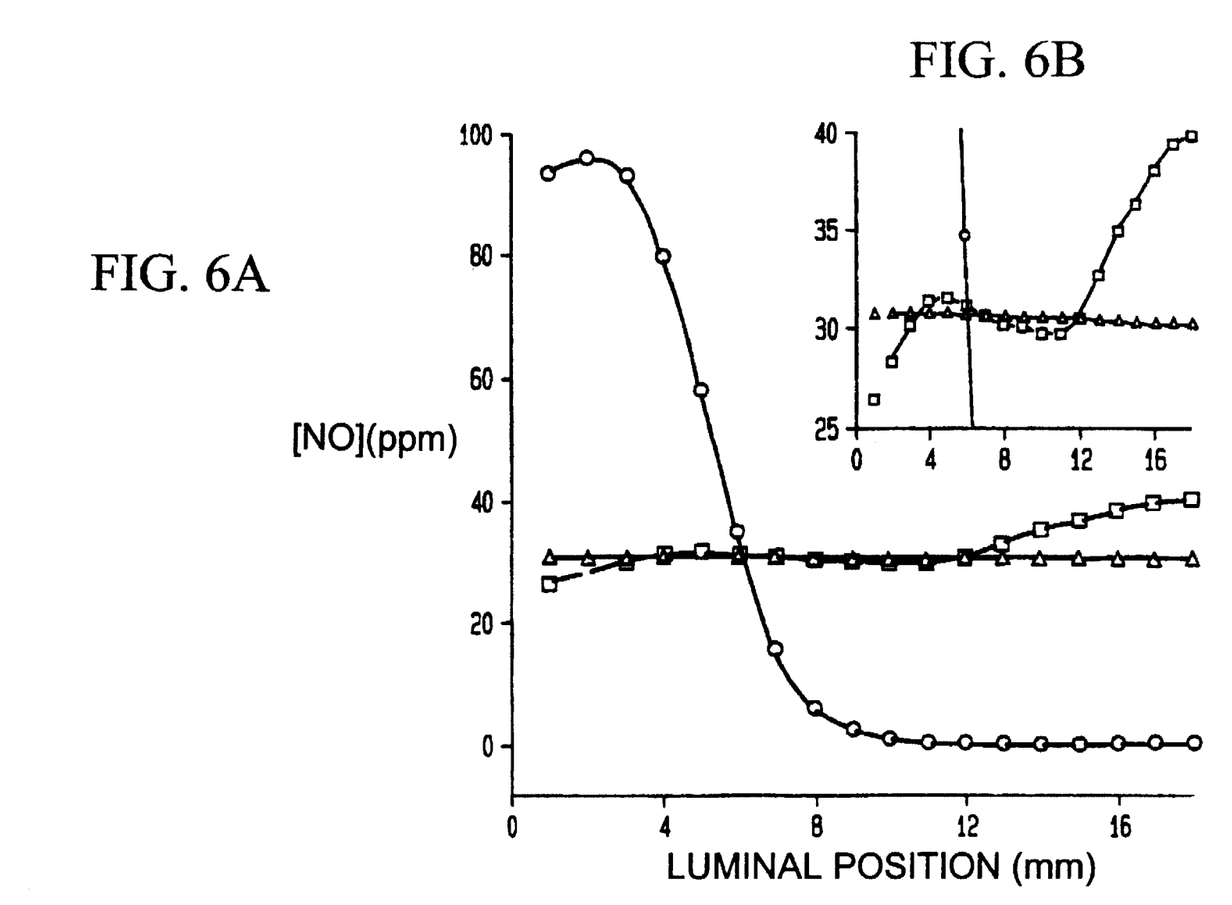
FIG. 6 illustrates nitric oxide concentrations ([NO]) along the tubing's cross sectional diameter measured at a fixed distance (12 cm) from the nitric oxide infusion port under the following different conditions: without an in-line mixing device, with a flow transducer cartridge in-line, and with a diaphragm mixing device in-line. A corrugated adult breathing circuit is using for testing. Nitric oxide flows from the stock cylinder at 150 ml/min into nitrogen flowing at 9800 ml/min. Assuming that complete mixing occurs, the predicted [NO] is about 30 ppm. Axis range changes and axis scale changes are made to create the graph insert which highlights a selected area of the larger graph. This

The gas mixing efficacy of the flow transducer cartridge when compared to the diaphragm device is shown in FIG. 6. Nitric oxide concentrations across the tubing cross sectional diameter without a mixing device are shown for comparison. FIG. 6 shows improved yet incomplete mixing of the gases with the flow transducer cartridge. The [NO] standard deviations for the different mixing strategies are as follows: tubing only, 38.0 ppm, flow transducer cartridge, 3.8 ppm; diaphragm device, 0.2 ppm.

Figure 7:
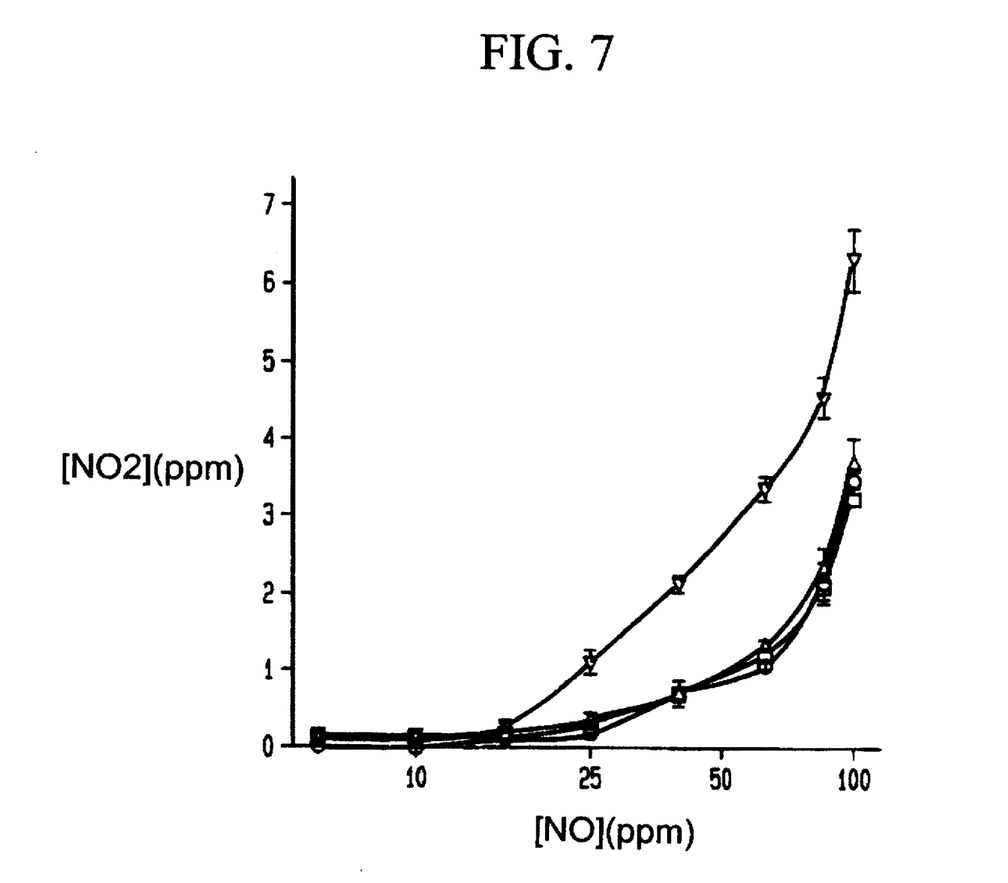

FIG. 7 shows the relationship between [$NO_2$] and both [NO] and methods of nitric oxide delivery. Nitrogen dioxide concentrations re measured at the ventilator Y-piece and are dependent upon [NO] ($F=1245.1$, $df=7$, $p<0.0001$; power with 0.05 $\alpha=1.000$), nitric oxide delivery methods ($F=432.8$, $df=3$, $p<0.0001$; power with 0.05 $\alpha=1.000$), and interactions between [NO] and nitric oxide delivery methods ($F=46.3$, $df=21$, $p<0.0001$; power with 0.05 $\alpha=1.000$). Nitrogen dioxide production with both the blending method ($p<0.05$) and the 76 cm distance method ($p<0.05$) are higher than the other two methods tested.

TABLE 1

Tubing Shape Effects on Mixing

| Luminal Position (mm) | Smooth Tubing | Corrugated Tubing |
|---|---|---|
| 1 | 21.6 | 21.2 |
| 2 | 21.8 | 20.8 |
| 3 | 20.3 | 20.1 |
| 4 | 18.7 | 18.8 |
| 5 | 17.2 | 17.7 |
| 6 | 15.6 | 16.6 |
| 7 | 13.6 | 16.1 |
| 8 | 12.3 | 16.1 |
| 9 | 12.9 | 16.6 |
| 10 | 13.5 | 16.6 |

Sampling is performed 21.3 cm from the nitric oxide infusion port. Both the smooth tubing and the corrugated tubing measure 10 mm in diameter. Nitric oxide flowed at a rate of 104 ml/mn from a 1986 ppm stock cylinder into nitrogen flowing at 10.6 l/min resulting in a predicted 19 ppm nitric oxide concentration.

It is well known that safe and efficacious nitric oxide administration predicates delivery of accurate [NO]. It is believed that this Example I reveals that accurate [NO] can be measured only after the stock nitric oxide gas is thoroughly mixed with the ventilated subject's breathing gases. At the flow rates tested, it is not possible to detect changes in gas mixing with changes in nitric oxide infusion flow rates. Nevertheless, increasing the stock nitric oxide flow may eventually lead to increased mixing thoroughness. Such an approach is feasible with lower stock [NO], yet increasing the stock nitric oxide flow to total flow ratio is believed to be counterproductive. Increases in the stock nitric oxide flow to total flow ratio is believed to decrease the maximum inspired oxygen fraction that can be achieved.

The results of this Example I appear to reveal that [NO] delivery estimate errors are dependent upon infusion port to sampling port distances. The numerous combinations of tubing sizes, tubing styles, and flow rates that are commonly used with constant flow ventilation systems complicates attempts to standardize the sampling port to infusion port distances. The equation used herein relates [NO] standard deviations to tubing distances {distance (cm)=31.2–27.8 ($\log_{10}$[NO|s.d.)+6.12 ($\log_{10}$[NO|s.d.)$^2$} and is specific for a 12 l/min total flow rate and the Hudson corrugated 10 mm i.d. tubing. For those health care providers who prefer to simply use tubing distance as a mixing strategy, the equation may provide a rough estimate of the minimum necessary distance for a chosen mixing thoroughness. For example, if the desired standard deviation for a predicted 19 ppm [NO] is ±1.00 ppm, then the calculated minimum distance needed is 31.2 cm. Similarly, if the desired standard deviation for a predicted 19 ppm [NO] is ±0.10 ppm, then the calculated distance needed is 65.1 cm. These distances will be longer if the following conditions occur: the total flow is less than 12 l/min, the internal tubing diameter is greater than 10 mm, or the tubing is smooth instead of corrugated.

It is believed that the presence of internal tubing corrugations increase gas mixing. Gas stagnation by some brands of internally corrugated tubing, such as those with deep corrugations, seems possible however. Gas stagnation may result in elevated inspired [$NO_2$]. It is believed, however, that corrugations in neonatal breathing circuits do not cause increases in [$NO_2$]. It is therefore believed that the choice of corrugated versus smooth breathing circuit tubing should be guided by, for instance, the specific mixing strategy used and by knowledge of gas flow characteristics of the specific breathing circuit used.

Many problems associated with designing a safe nitric oxide administration system are believed to be avoided with the use of a mixing device of the present invention. Of the two mixing devices discussed in this Example I, the diaphragm device mixed the gases most thoroughly. Both devices adapted easily to 10 mm i.d. ventilation tubing; however, the diaphragm device is smaller, believed to generally be less expensive to manufacture, and permits nitric oxide infusion closer to the Y-piece. The diaphragm device also has no moving parts whereas the flow-transducer cartridge has a moving part.

This Example I is believed to show that the [$NO_2$] production is greater with higher [NO]. It also shows, however, that [$NO_2$] measured at the Y-piece are dependent upon the mixing strategy selection. In general, infusing nitric oxide into the ventilation system closer to the Y-piece results in lower [$NO_2$] measured at the Y-piece. The difference between [$NO_2$] measured with the mixing device method and the 38 cm tubing distance method is not believed to be significant. If the equation relating tubing distance and standard deviation is solved for $\log_{10}$ standard deviation [$\log_{10}$standard deviation=1.57–0.0539 (distance) +0.000205 (distance)$^2$], the [NO] delivery estimate error can be calculated due to laminar flow. Because a total flow rate of approximately 12 l/min is used and the corrugated neonatal breathing circuit, it delivers 19.0 ppm to the Y-piece with an error due to laminar flow of approximately 0.66 ppm. If this delivery estimated error due to laminar flow is acceptable, similar corrugated neonatal tubing is used, and the total flow rate is maintained above 12 l/min, then the 38 cm tubing distance method of gas mixing represents gas delivery method of choice.

Since minimizing [NO] delivery estimate errors and toxic byproduct exposure is desired, it is believed that the present invention minimizes [$NO_2$] measured at the Y-piece. By allowing nitric oxide infusion ports to be close to the Y-piece, mixing devices of the present invention are believed to decrease the exposure to toxic byproducts during nitric oxide inhalation.

Moreover, the results of this Example I suggest that commonly used gas flow rates favor streaming within constant flow ventilation systems. Measuring [NO] variations along the cross sectional diameter of the ventilation tubing provides an effective laminar flow detecting mechanism. Calculating [NO] standard deviations using measurements from along the cross sectional diameter are useful representations of the potential [NO] delivery estimate errors. Toxic byproduct exposure during nitric oxide inhalation is dependent upon both the [NO] and the nitric oxide delivery method.

EXAMPLE II

Comparison of [NO] across Laminar Flow Gradient With and Without Gas Mixing Device In this Example II, the breathing circuit assembly designated as 70 in FIGS. 10A & B is connected to a nitrogen gas supply line which feeds nitrogen in the mainstream at a flow rate of 10 L/min. The administration port 75 is connected to a new stock cylinder which contains about 1985 ppm nitric oxide. The breathing circuit assembly is tested with a gas mixing device illustrated in FIG. 2, a gas mixing device containing a flow transducer, designated as Product No. 9230, and distributed by Bird Products Corporation, Palm Springs, Calif. (as opposed to a diaphragm), and without a gas mixing device. The sampling port 77 is positioned downstream of gas mixing device 20 and about 12 cm from the administration port 75, which is positioned upstream from gas mixing device 20, for sampling the gas mixtures and to test for [NO] across the laminar flow gradient as the gas mixture exits the breathing circuit assembly 70. To test [NO] in the laminar flow of the gas mixture across the hollow inspirator tubing, a needle is introduced into the sampling port 77 and moved to 18 different positions in mm increments for sampling the [NO] at each position. The test results are reported below in Table 2 and illustrated in FIG. 6.

TABLE 2

| Needle Position in mm Increments | Straight Tubing (No Gas Mixing Device) | Bird Transducer Gas Mixing Device | Gas Mixing Device in FIG. 2 |
| --- | --- | --- | --- |
| 0 | 93.1 | 26.5 | 30.7 |
| 1 | 95.8 | 28.4 | 30.7 |
| 2 | 92.6 | 30.1 | 30.7 |
| 3 | 79.0 | 31.3 | 30.7 |
| 4 | 57.7 | 31.5 | 30.7 |
| 5 | 34.6 | 31.0 | 30.6 |
| 6 | 15.9 | 30.5 | 30.6 |
| 7 | 6.1 | 30.1 | 30.6 |
| 8 | 2.6 | 30.0 | 30.5 |
| 9 | 1.0 | 29.6 | 30.5 |
| 10 | 0.4 | 29.6 | 30.5 |
| 11 | 0.3 | 30.5 | 30.4 |
| 12 | 0.3 | 32.6 | 30.4 |
| 13 | 0.3 | 34.9 | 30.3 |
| 14 | 0.3 | 36.2 | 30.2 |
| 15 | 0.4 | 38.0 | 30.2 |
| 16 | 0.5 | 39.3 | 30.2 |
| 17 | 0.5 | 39.8 | 30.2 |

EXAMPLE III

Comparison of [NO] Across Laminar Flow Gradient Using Gas Mixing Device Equipped With and Without A Stem and a Hollow 4 mm Aperture Hub In this Example III, the laminar nitric oxide concentration across the flow gradient is measured in a hollow 22 mm internal diameter corrugated ventilator tubing using the gas mixing device illustrated in FIG. 2, with and without a stem, which is assembled into a breathing circuit assembly illustrated in FIGS. 11A & B.

The ventilator flow of nitrogen gas in the mainstream is at about 6 L/min or about 3 L/min, and the flow rate from a new stock cylinder containing about 1964 ppm nitric oxide and about 0.42 ppm nitrogen dioxide is at about 100 cc/min. The mixture of nitric oxide and nitrogen dioxide is introduced into breathing circuit assembly 80 at administration port 91. Administration port 91 is positioned upstream from the gas mixing device 20 and about 12 cm from sampling port 90, which is positioned downstream from gas mixing device 20. A needle is introduced into sampling port 90 and into the hollow inspiratory tubing at ten different positions selected in mm increments for sampling the [NO] across the laminar flow gradient in the mixture of gases exiting from the gas mixing device 20 in breathing circuit assembly 80. The results are reported below in Table 2.

TABLE 3

| Needle Position in mm Increments | Without Stem @ 6.0 L/min $N_2$ | With Stem @ 6.0 L/min $N_2$ | With Stem @ 3.0 L/min $N_2$ | Without Stem @ 3.0 L/min $N_2$ |
| --- | --- | --- | --- | --- |
| 1 | 32.9 | 32.4 | 64.6 | 64.6 |
| 2 | 32.8 | 32.4 | 64.2 | 64.4 |
| 3 | 32.7 | 32.3 | 64.0 | 64.1 |
| 4 | 32.5 | 32.2 | 63.6 | 63.4 |
| 5 | 32.3 | 32.2 | 62.7 | 62.8 |
| 6 | 32.1 | 32.1 | 61.8 | 61.8 |
| 7 | 32.0 | 32.0 | 61.7 | 61.6 |
| 8 | 31.9 | 31.9 | 61.6 | 61.6 |
| 9 | 31.9 | 31.8 | 61.6 | 61.6 |
| 10 | 31.9 | 31.8 | 61.7 | 61.7 |

The present invention may, of course, be carried out in other specific ways than those herein set forth without departing from the spirit and essential characteristics of the invention. The present embodiments are, therefore, to be considered in all respects as illustrative and not restrictive and all changes coming within the spirit and scope of the appended claims are intended to be embraced herein.

Having described our invention, we claim:

1. A gas mixing device for use in a breathing system for receiving more than one gas and thoroughly mixing the received gases before the gases are inhaled by a subject, said gas mixing device being adapted to be connected to a hollow breathing tube or a hollow breathing tube Y-piece of the breathing system and comprising:

gas receiving means for receiving more than one gas at the same time; and turbulence means for generating a pressure gradient to create turbulence in said gas receiving means when the gases enter into said gas receiving means, so that the gases entering into and passing through said gas receiving means are thoroughly mixed to provide a flow of mixed gases, as opposed to a laminar flow of gases, downstream from said gas mixing device for inhalation by a subject.

2. A gas mixing device of claim 1, said gas mixing device being connected to a hollow breathing tube.

3. A gas mixing device of claim 1, said gas mixing device being connected to a hollow breathing Y-piece.

4. A gas mixing device of claim 1, said gas receiving means defining a chamber having a hollow interior.

5. A gas mixing device of claim 4, said turbulence means being a diaphragm having an aperture therein, said diaphragm being connected to said chamber and said aperture in said diaphragm being in communication with the hollow interior of said chamber, the pressure gradient being across said diaphragm.

6. A gas mixing device of claim 4, said aperture having a diameter of between about 4 mm and about 10 mm.

7. A gas mixing device of claim 5, said diaphragm having a stem connected thereto, said stem having a hollow interior and being in communication with the aperture.

8. A gas mixing device of claim 7, said aperture having a diameter of between about 4 mm and about 10 mm.

9. A gas mixing device of claim 1, said turbulence means being a restrictor for restricting the flow of the gases into said gas chamber means.

10. A gas mixing device of claim 1, said gas mixing device further including an administration port positioned upstream from said turbulence means for introducing into said gas receiving means a gas.

11. A gas mixing device of claim 1, the gas being nitric oxide.

12. A gas mixing device of claim 1, the gas being selected from the group consisting of oxygen, air, nitrous oxide, nitrogen, carbon dioxide, chloroform, halothane, isoflurane, enflurane and methoxyflurane.

13. A gas mixing device of claim 1, said gas mixing device further including a sampling port for sampling the mixture of gases which have passed through said gas mixing device.

14. A breathing circuit assembly for use in a breathing system for receiving more than one gas and thoroughly mixing the received gases before the gases are inhaled by a subject, said breathing circuit assembly comprising:

gas receiving means for receiving more than one gas at the same time; and turbulence means for generating a pressure gradient to create turbulence in said gas receiving means when the gases enter into said gas receiving means, so that the gases entering into and passing through said gas receiving means are thoroughly mixed to provide a flow of mixed gases, as opposed to a laminar flow of gases, downstream from said gas mixing device for inhalation by a subject;

an administration port located upstream from but in close proximity to said turbulence means for introducing a gas into said gas receiving means, said breathing circuit assembly being adapted to be connected to a hollow inspiratory tube from which other gases may flow; and a hollow inspiratory tube with which said gas mixing device and said administration port are in communication and from which a subject inhales the thoroughly mixed gases.

15. A breathing circuit assembly of claim 14, said breathing circuit assembly further including a sampling port located downstream from said gas receiving means for sampling gases passing through said gas mixing device.

16. A breathing circuit assembly of claim 14, said breathing circuit assembly being connected to a hollow breathing Y-piece.

17. A breathing circuit assembly of claim 10, said hollow inspirator tube being a part of a hollow breathing Y-piece.

18. A breathing circuit assembly for use in a breathing system for receiving more than one gas and thoroughly mixing the received gases before the gases are inhaled by a subject, said breathing circuit assembly comprising:

gas receiving means for receiving more than one gas at the same time; and turbulence means for generating a pressure gradient to create turbulence in said gas receiving means when the gases enter into said gas receiving means, so that the gases entering into and passing through said gas receiving means are thoroughly mixed to provide a flow of mixed gases, as opposed to a laminar flow of gases, downstream from said gas mixing device for inhalation by a subject;

an administration port located upstream from but in close proximity to said turbulence means for introducing a gas into said gas receiving means, said breathing circuit assembly being adapted to be connected to a hollow breathing Y-piece from which other gases may flow; and a hollow breathing Y-piece with which said gas mixing device and said administration port are in communication.

19. A breathing circuit assembly of claim 18, said breathing circuit assembly further including a sampling port positioned downstream from said gas receiving means for sampling gases passing through said gas mixing device.

20. A method for allowing a thoroughly mixed mixture of breathable gases to be delivered to a subject via a breathing system, said method comprises:

passing more than one gas through a gas mixing device, the gas mixing device being assembled into a breathing system and comprising:

gas receiving means for receiving more than one gas at the same time; and turbulence means for generating a pressure gradient to create turbulence in said gas receiving means when the gases enter into said gas receiving means, so that the gases entering into and passing through said gas mixing device are thoroughly mixed to provide a flow of mixed gases, as opposed to a laminar flow of gases, downstream from said gas mixing device; and delivering the thoroughly mixed gases to the subject.

21. A method of claim 20, one said gas being nitric oxide.

22. A method of claim 20, said gases being selected from a group consisting of oxygen, air, nitrous oxide, nitrogen, carbon dioxide, chloroform, halothane, isoflurane, enflurane and methoxyflurane.

23. A method of claim 20, said method including the further step of locating an administration port upstream from but in close proximity to the turbulence means for introducing a first gas into a mainstream of at least a second gas flowing into the turbulence means for thoroughly mixing the first and second gases in the gas receiving means.

24. A method of claim 23, the first gas being nitric oxide and the second gas being oxygen.

25. A method of claim 23, said method including the further step of locating a sampling port downstream from the gas receiving means for sampling the mixture of the first and second gases flowing from the gas receiving means.

* * * * *